United States Patent [19]

Mickiewicz et al.

[11] Patent Number: 4,693,254

[45] Date of Patent: Sep. 15, 1987

[54] TRANSCUTANEOUS NERVE STIMULATION DEVICE USING A COMMON CONTROLLER FOR PULSE PRODUCTION AND PARAMETER DISPLAY

[75] Inventors: Stanley P. Mickiewicz, Stoughton; Alan Coombes, Hingham, both of Mass.

[73] Assignee: Codman & Shurtleff, Inc., Randolph, Mass.

[21] Appl. No.: 910,271

[22] Filed: Sep. 17, 1986

Related U.S. Application Data

[63] Continuation of Ser. No. 617,442, Jun. 5, 1984, abandoned.

[51] Int. Cl.⁴ ............................................. A61N 1/32
[52] U.S. Cl. .................................................. 128/421
[58] Field of Search ............... 428/419 F, 420, 420 R, 428/421, 422, 423 W

[56] References Cited

U.S. PATENT DOCUMENTS

| | | | |
|---|---|---|---|
| 4,071,033 | 1/1978 | Nawracaj et al. | 128/422 |
| 4,102,348 | 7/1978 | Hihara et al. | 128/422 |
| 4,147,171 | 4/1979 | Greene et al. | 128/421 |
| 4,177,819 | 12/1979 | Kofsky et al. | 128/422 |
| 4,210,152 | 7/1980 | Berry | 128/422 |
| 4,237,899 | 12/1980 | Hagfors et al. | 128/422 |
| 4,249,537 | 2/1981 | Lee et al. | 128/422 |
| 4,520,825 | 6/1985 | Thompson et al. | 128/422 |

Primary Examiner—Lee S. Cohen
Assistant Examiner—David Shay
Attorney, Agent, or Firm—W. Brinton Yorks, Jr.

[57] ABSTRACT

A transcutaneous nerve stimulation device is provided using a common controller for both output pulse production and treatment parameter display. The common controller, which preferentially takes the form of a programmed microprocessor, is connected by signal lines to both the pulse output circuitry and the display, which are controlled by time-sharing the signal lines. The controller is responsive to operator entered input signals for the calculation of output pulse characteristics and display parameters. During a majority of treatment time, the controller is providing signals on the signal lines for control of the display. The display signals are interrupted during timed intervals when output signals are produced.

18 Claims, 15 Drawing Figures

TRANSCUTANEOUS NERVE STIMULATION DEVICE USING A COMMON CONTROLLER FOR PULSE PRODUCTION AND PARAMETER DISPLAY

This is a continuation of application Ser. No. 617,442, filed June 5, 1984, now abandoned.

This invention relates to transcutaneous nerve stimulation devices and, in particular, to such devices in which output and display signals are controlled by a common processor.

Transcutaneous nerve stimulation devices apply stimulating electrical pulses to electrodes which contact the skin of a patient to relieve pain through electrical nerve stimulation. A patient will generally be given a device by a physician, together with instructions on how to use the device safely and effectively. Thereafter, the patient uses the device to perform the necessary treatment. Accordingly, it is desirable for the device to be simple and easy for the patient to use.

It has been found that different patients receive benefit from different types of pulse sequences. Hence, a stimulation device should be capable of providing a range of different types of pulse sequences, so that the physician can prescribe the treatment most beneficial to any particular patient.

In many circumstances it may be possible for the patient to use the stimulation device while continuing his or her normal daily activities. To permit this, the device must be small and portable. A device small enough to slip into a pocket and light enough to be carried on a patient's belt is therefore desirable.

To perform treatment, the patient should be able to select his prescribed treatment pulse sequence using simple controls, and must verify the treatment sequence by observing an indicator or display on the device. In such a device, then, electronic circuitry must be provided to control the treatment pulse sequence and to control the display. However, the provision of separate circuit assemblies for these two functions increases the size of the device, and can result in a large, bulky stimulation device which opposes the desire for portability. Thus, it is desirable for a stimulation device to employ common control circuitry for both output pulse production and treatment parameter display.

In accordance with the principles of the present invention, a stimulation device is provided using a common controller for both output pulse production and treatment parameter display. The common controller, which preferentially takes the form of a programmed microprocessor, is connected by signal lines to both the pulse output circuitry and the display, which are controlled by time-sharing the signal lines. The controller is responsive to operator entered input signals for the calculation of output pulse characteristics and display parameters. During a majority of treatment time, the controller is providing signals on the signal lines for control of the display. The display signals are interrupted during timed intervals when output signals are produced. The output signal timing is governed in a manner such that the desired pulse sequences are produced without any noticeable effect on the display, which prolongs the life of the power supply and the display device.

Figure 1:
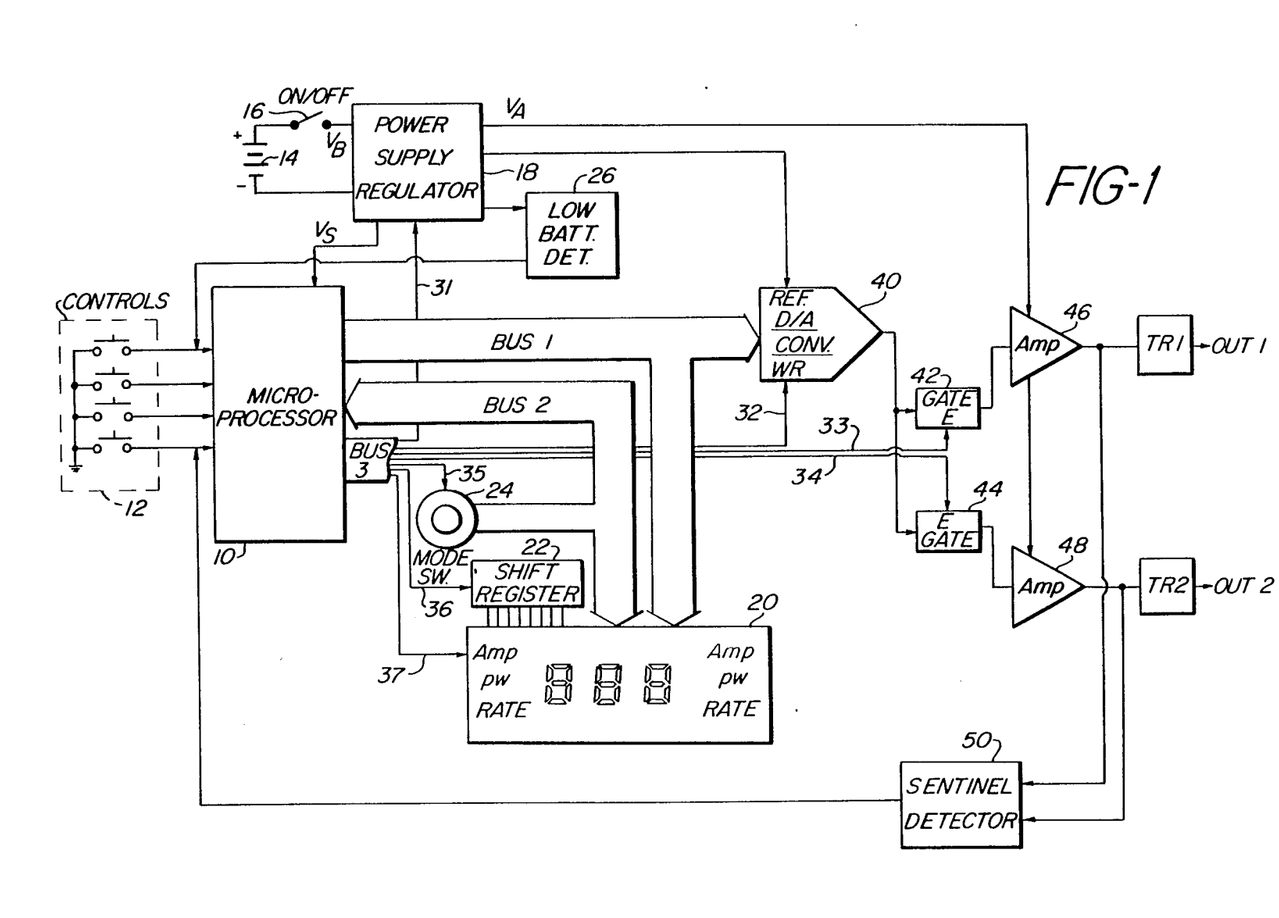
FIG. 1 is a schematic illustration of a stimulation device constructed in accordance with the principles of the present invention.

Referring to FIG. 1, a schematic illustration of a digitally-controlled stimulation device constructed in accordance with the principles of the present invention is shown. A microprocessor 10 receives operator input control signals from pushbutton switches shown at 12. The microprocessor also receives inputs from a low battery detector 26 and a sentinel signal detector 50. Signals from either of these two latter sources will precipitate a termination of output pulse production.

The device is powered by a battery 14, which is connected to a power supply regulator 18 by an on/off switch 16. The regulator 18 provides regulated supply voltage $V_S$ for the microprocessor 10, output stage voltage $V_A$, and a reference voltage for a digital-to-analog (D/A) converter 40. The regulator is also coupled to the low battery detector 26 for voltage sampling by the detector.

The microprocessor 10 has two ports and a data bus, shown as bus 1, bus 2, and bus 3. Bus 1 provides a digital words representative of output signal levels to the D/A converter 40, and also control signals for segments of the right-most digit of a display 20. Bus 2 provides control signals for segments of the center digit of the display 20, and also samples the setting of a mode switch 24. Bus 3 has a plurality of data lines for dedicated control functions. Line 31 controls the timing of the application of the reference voltage to the D/A converter 40. Line 32 controls the clocking of an output voltage level word into the buffer of the D/A converter. Lines 33 and 34 control the closings of gates 42 and 44, which couple the voltage from the D/A converter to the outputs of the device. Line 35 applies a signal to the mode switch 24 during the time that the state of the mode switch is sampled. Line 36 applies input data to a shift register 22, and line 37 turns on the AMP indicator on the left side of the display 20 when the amplitude of pulses at the first output is being displayed numerically.

The output of the D/A converter is coupled by way of the two CMOS gates 42 and 44 to inputs of output signal amplifiers 46 and 48. The outputs of the amplifier 46 and 48 are coupled to respective output transformers TR1 and TR2, and to inputs of the sentinel signal detector 50. A portion of the schematic diagram of FIG. 1 is shown in further detail in FIG. 2. The microprocessor 10, which may be of the generic type designated 80C49, is shown with its inputs and outputs specifically designated. A 3 MHz crystal 101 is coupled across inputs X1 and X2 of the microprocessor 10. A capacitor 103 couples the reset input of the microprocessor to ground so that the microprocessor will receive a reset command immediately after the device is turned on and the supply voltage has stabilized. Four pushbutton controls, labelled DISP, INC, DEC and SET are coupled to inputs T0, T1 and the interrupt input of the microprocessor. A number of diodes are used to encode signals from the pushbutton switches. For instance, when the DISP pushbutton is closed to change the function being displayed on the display, the diodes from the DISP pushbutton apply low (ground level) signals to the T∅ and T1 inputs. The microprocessor will then decode these two low lines as a DISP command. Also coupled to microprocessor inputs are a sentinel signal by way of transistor 105, and a low battery detection signal. A power on initializing signal is coupled to input T1.

Figure 2:
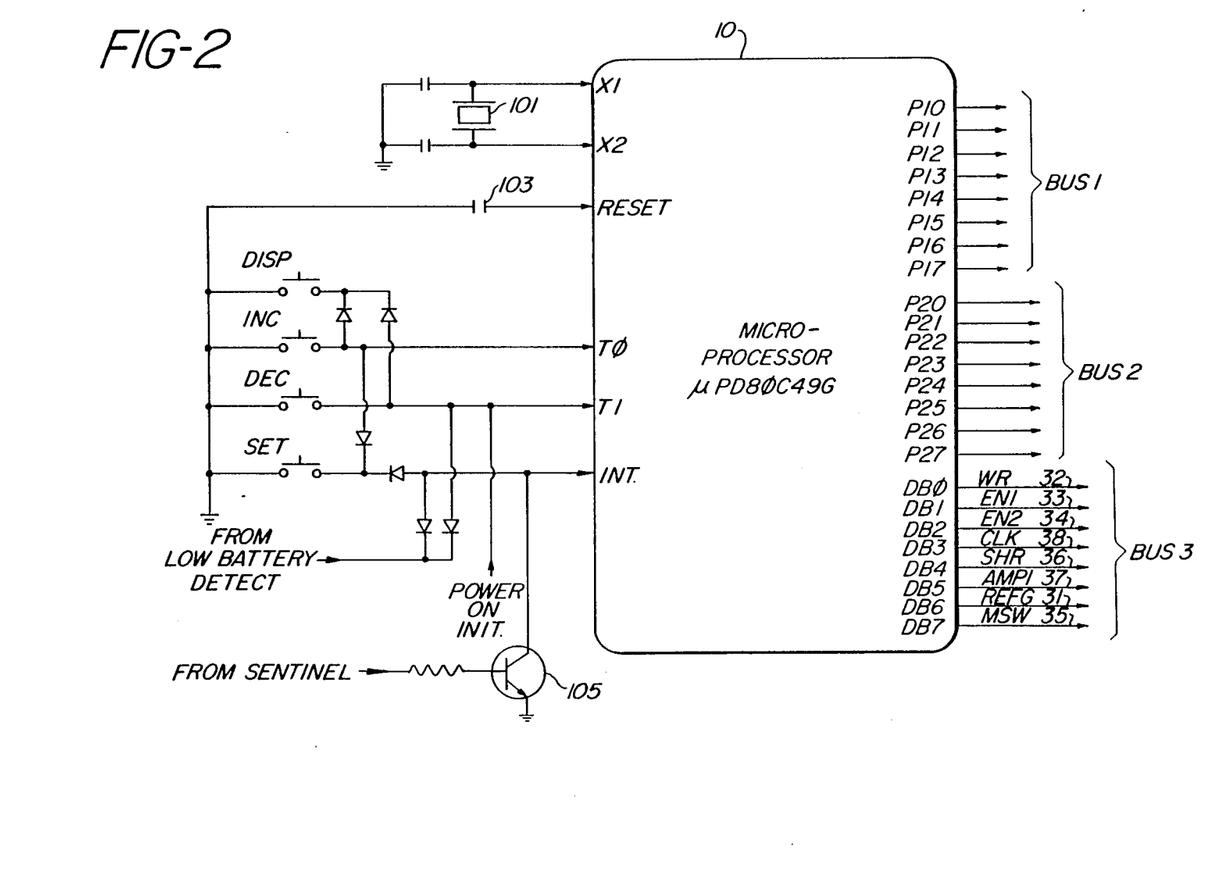
FIGS. 2, 3, and 4 are more detailed schematics of the illustration of FIG. 1.

The individual lines of the three buses are also shown. Buses 1 and 2 are ports of eight lines each, and bus 3 comprises eight data lines for controlling the specific functions enumerated above. Line 38, which was not shown in FIG. 1, is a clock line which is selectively activated to load data from line 36 into the shift register 22.

Figure 3:
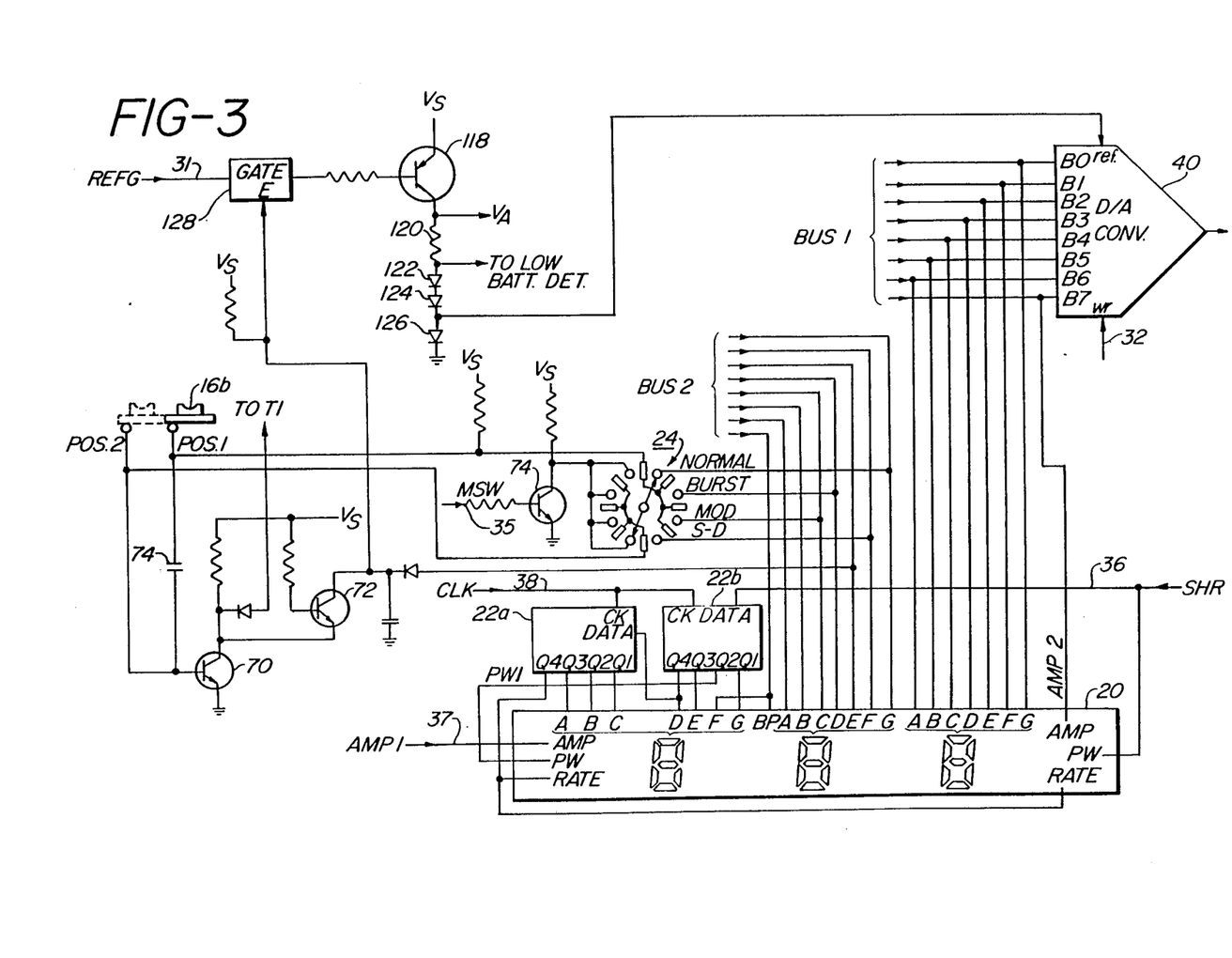

FIG. 3 illustrates the display and bus arrangement of FIG. 1 in further detail. Line 31 from the microprocessor is coupled through a CMOS gate 128 to the base of a transistor 118. A signal REFG on this line 31 turns on transistor 118 to apply a reference voltage to D/A converter 40 when needed during activation of the D/A converter. When the D/A converter is not supplying an output voltage, the reference voltage is not needed and is turned off by the REFG signal to conserve battery power. The reference voltage is otherwise turned on momentarily every half second to sample the battery voltage. The gate 128 will be interrupted momentarily after the on/off switch 16 is turned on while capacitor 74 charges. The time for the capacitor to charge allows the system to stabilize before transistor 70 is turned off, at which time the T1 input of the microprocessor is released. When T1 is released, the output pulses are at a low, safe level. Transistor 72 in turn will turn off, releasing the enabling line to gate 128. Transistor 72 also forces a mode change to the desired mode. The application of reference voltage to the A/D converter may then proceed, as the microprocessor is running with valid data. This hold-off sequence prevents the application of inaccurate, high-level output pulses to the patient after a momentary turning off of power, which could leave spurious data in the microprocessor registers until the registers have been validly restored.

When the mode switch 24 is to be interrogated to determine if a change in mode has occurred, a signal MSW on line 35 momentarily turns on a transistor 74. The arm of the mode switch 24 will then apply a low signal level to the output of the switch to which it is presently connected. This low signal level is detected on the corresponding one of the four lines of bus 2 to which the mode switch is connected. Bus 2 is acting as a data input port at that time. During the remainder of the time, bus 2 is providing segment drive signals for the middle digit of the display 20 and a backplane (BP) signal. Bus 1 is providing segment drive signals for the right-most digit of the display at all times except when the D/A converter 40 is being loaded with output signal level data.

Shift register 22, which is comprised of two four-bit, serially connected shift registers 22a and 22b, is loaded with data for the left-most display digit from line 36. The clock signal on line 38 shifts the data into the shift registers 22a, 22b. The display also displays the indicators AMP, PW, and RATE on either side to tell the operator which parameter is being controlled by the INCREASE and DECREASE pushbuttons. The left indicators correspond to output 1 and the right indicators to output 2. The AMP indicator for output 1 is controlled by the AMP1 signal on line 37, and the AMP indicator for output 2 is controlled by one line of bus 1.

The PW (pulse width) indicator for output 1 is controlled by the Q2 location of shift register 22b, and the PW indicator for output 2 is time-shared on line 36. The RATE indicators are commonly controlled by the Q4 location of shift register 22a, as both outputs will exhibit the same pulse rate, or frequency.

Figure 4:
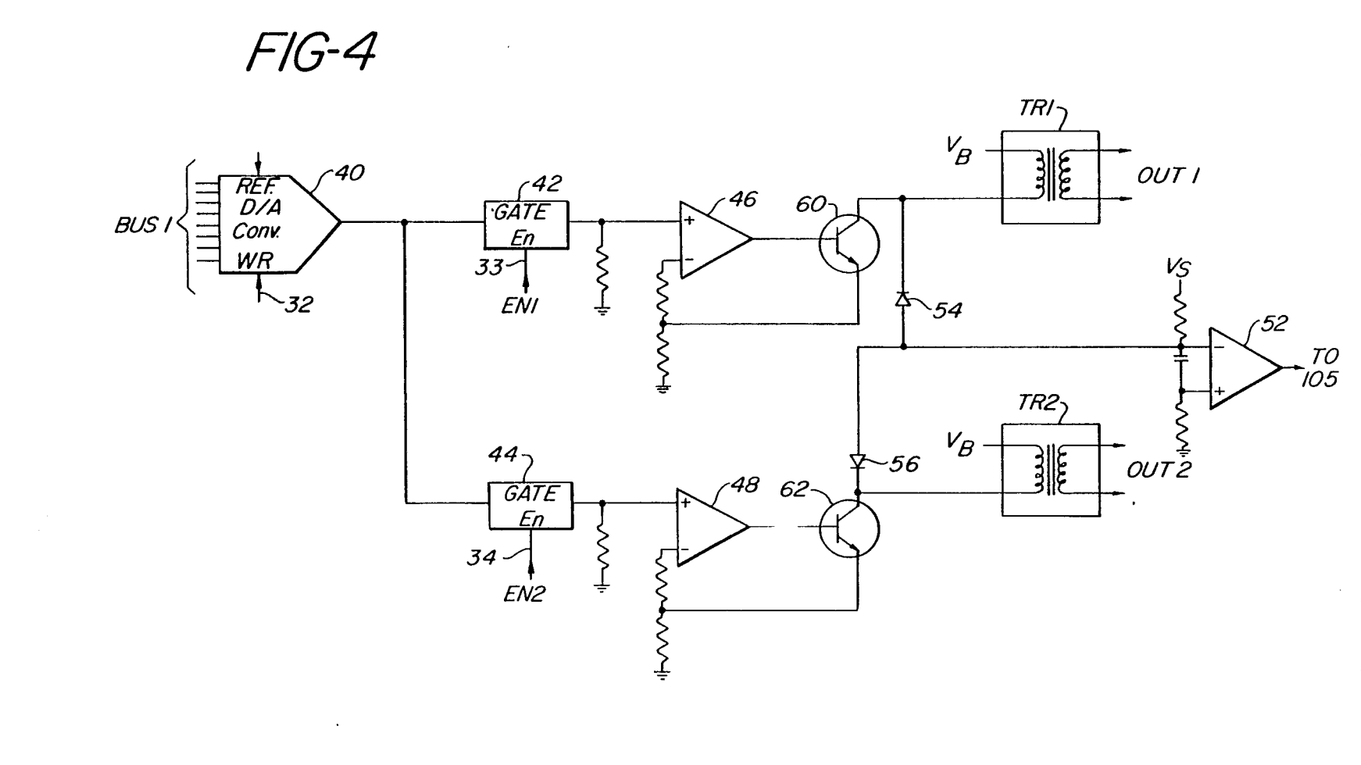

The output section of the stimulation device is shown in detail in FIG. 4. When the D/A converter is producing the desired output level, signals EN1 and EN2 on lines 33 and 34 render CMOS gates 42 and 44 conductive for periods corresponding to the operator-entered pulse width settings. Output pulses are then applied to amplifiers 46 and 48. Output transistors 60 and 62 are turned on to apply output signals to output transformers TR1 and TR2. The output pulses are then transformer coupled to leads connected to electrodes (not shown) on the skin of the patient.

Before each transmission of output pulses, test pulses called sentinel pulses are transmitted to verify that the electrodes are properly connected to the patient. If the connections are properly made, the pulses will not exceed the trigger threshold of a comparator 52, and the output state of the comparator will not change. Improper electrode connections will cause detection of the sentinel pulses, which are coupled to the interrupt input of the microprocessor by transistor 105 (FIG. 2), and the microprocessor will be informed of the improper connections. The microprocessor will query its interrupt line, and will recognize the problem. A sentinel flag will be set, and the system will halt the production of output pulses until the failure is remedied and the device is restarted. The sentinel system is more fully described in concurrently filed U.S. patent application Ser. No. 617,429, entitled "TRANSCUTANEOUS NERVE STIMULATION DEVICE WITH SENTINEL".

Figure 5:
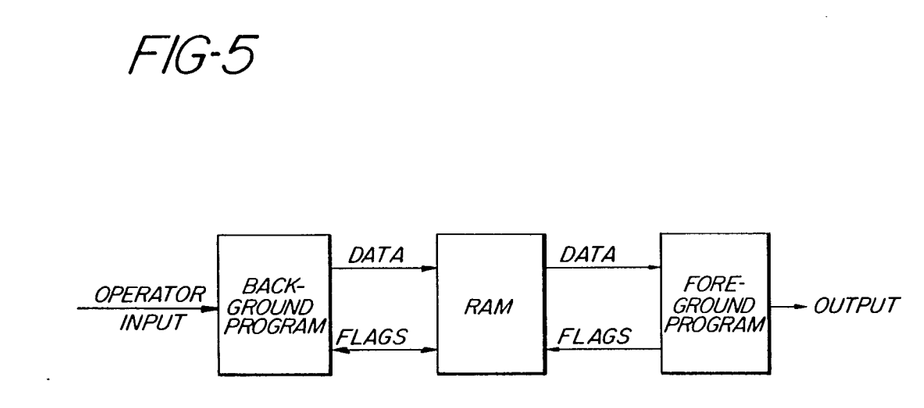
FIG. 5 is a block diagram of the controller of FIG. 1.

The software which controls the microprocessor, and hence operation of the device, is stored in a 2K read only memory (ROM). The software is partitioned into a foreground program and a background program. The two programs interact through an exchange of data words and flag bits stored in 128 bytes of random access memory (RAM). This software/hardware structure is shown in FIG. 5. During most of the time, the background program loop is running. The background program continuously monitors the pushbutton inputs and the mode switch, looking for a change. When a change occurs, it is detected and any variables which require change are calculated and stored in the RAM. The variables are then available for use by the foreground program.

An internal timer which runs continuously interrupts the background program every 2.5 msec. The foregound program, which controls precise timing functions, then proceeds through its sequence, producing output signals at the appropriate times. Output signals are produced in accordance with the data values that the foreground program finds in RAM locations. When the foreground program produces output signals from new data values it returns status flags to the RAM to indicate to the background program that the new data has been utilized.

Figure 6A:
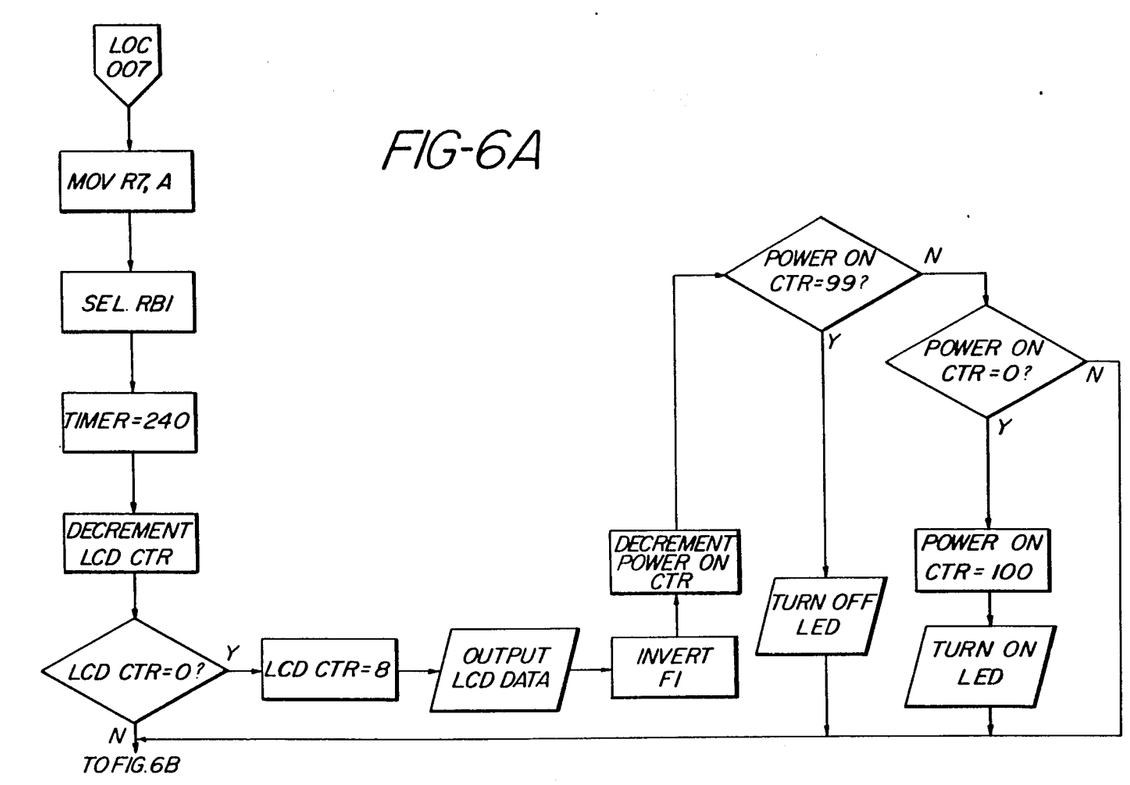
FIGS. 6A, 6B, 6C and 7 are flowcharts of the programming of the controller of FIG. 5.
Figure 6B:
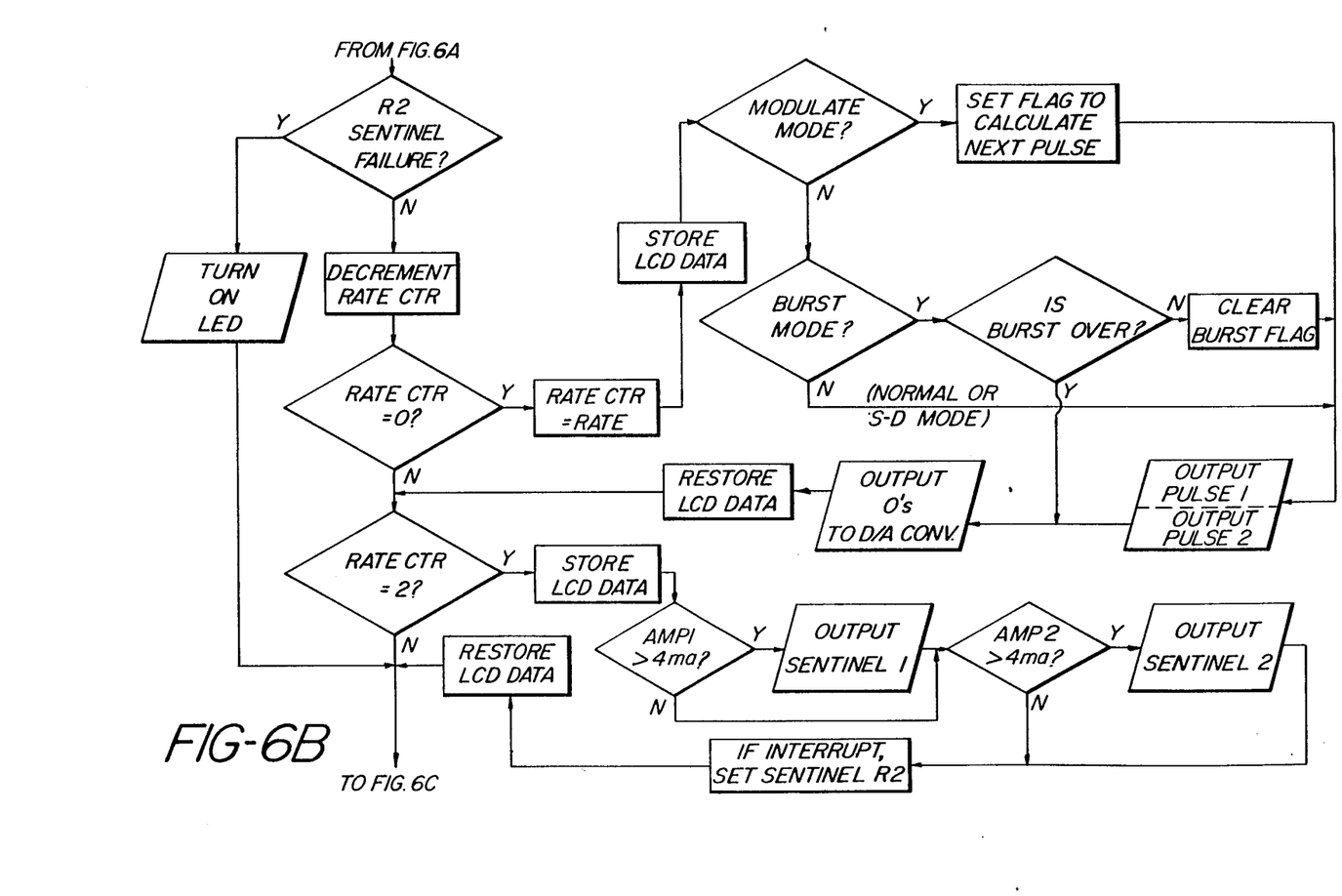
Figure 6C:
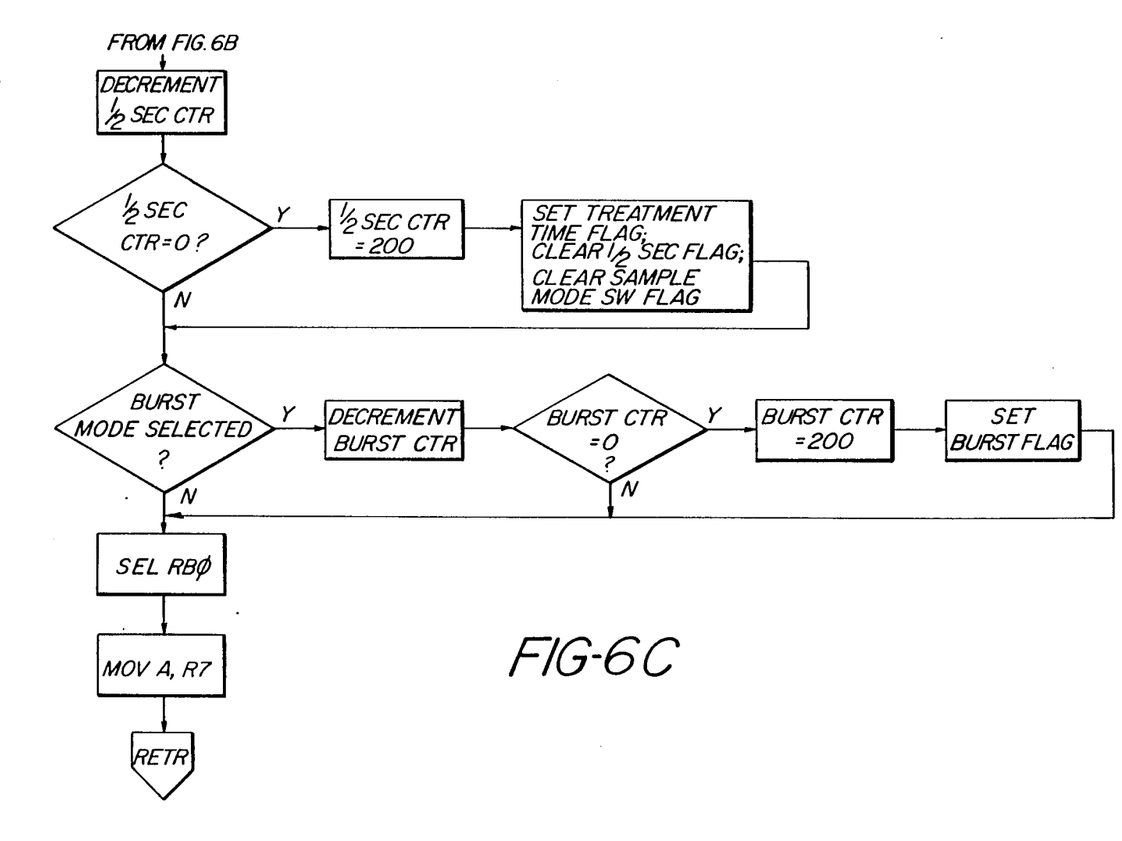

The foreground program is shown in flowchart form in FIGS. 6A, 6B, and 6C. When the internal times has reached zero after 2.5 msec, the background program is interrupted and the microprocessor goes to location 007, where the foreground program begins. The background program data in the accumulator is stored in register 7, and register bank 1 is selected for foreground program control. Register bank 1 contains a number of counters which are decremented by the foreground program to maintain the appropriate timing of output functions. The internal timer is initialized to a value of 240, corresponding to 2.5 msec, and the foreground processing begins.

The foreground program first decrements an LCD counter for control of the display. The LCD display receives two types of pulse trains: a common backplane pulse train and individual segment pulse trains, each of a frequency of 25 Hz. When the two pulse trains are changing in phase for any one display segment or indicator, there is no potential difference between the pulse trains and the segment or indicator is not displayed. When the two pulse trains are in phase opposition, however, there is always a voltage differential between them and the segment or indicator will be displayed.

When the LCD counter has been decremented to zero, a half cycle of the 25 Hz pulse rate has expired and the outputs to the LCD display must be changed. The LCD counter is initialized to a value of eight (8 times 2.5 msec = 20 msec = ½ cycle of 25 Hz), and LCD data resident in the RAM is put on buses 1 and 2. LCD data is serially loaded into the shift register 22 from data line 36. An invert flag F1 is set to inform the background program that it must calculate inverted LCD data values for the next half cycle (opposite phase) of the LCD pulse trains.

A Power On counter is decremented. Every two seconds a "power on" LED (light emitting diode) is flashed for 20 msec to indicate to the operator that the device is operating properly. The counter is first checked for a value of 99. At this value, the LED is turned off. The counter is then checked for a value of zero, at which time the LED is to be turned on. At zero the counter is reinitialized to a value of 100, the LED is turned on, and the foreground program continues in FIG. 6B.

A register R2 is then checked to see if a sentinel failure has been detected. If so, the LED is turned on continuously to alert the user of the problem. The LED can only be turned off by remedying the electrode problem and restarting the system.

The program next decrements the rate counter. The rate counter counts down from an initial value (RATE) which is a number calculated by the background program. The RATE number represents the interval between output pulses selected by the operator. If the rate counter has reached zero, output pulses are to be produced, and the counter is reinitialized and the LCD output data is stored. Since bus 1 will now be used for output data, the LCD data on that bus must be stored during this time, and restored on the bus after the output pulse sequence is finished.

The program first checks to see if the device is operating in the modulate mode. In this mode, each output pulse differs in pulse width and amplitude from the previous pulse. Hence, a flag is set to inform the background program that a pulse has been produced, and that new parameter values must be calculated for the following pulse. If the device is not in the modulate mode, the program checks to see if the device is in the burst mode. In the burst mode, a burst of seven pulses is produced every half second at a rate of 80 Hz. The amplitude of the burst pulses is determined by the operator. If the device is in the burst mode, the program checks to see if a pulse sequence is in progress. If the burst pulse sequence is over, no output is produced. If the sequence of seven pulses is not complete, a burst mode flag is cleared and pulse output commences.

When the program does not find the device to be operating in either the modulate or burst mode, the device must be operating in either the normal or the strength-duration mode. In either case, a repetitive sequence of treatment pulses is to be produced, and the program proceeds to produce output pulses. The microprocessor controls pulse production at the first output, then pulse production at the second output. At first, a REFG signal on line 31 applies a reference voltage to the D/A converter. A digital word is put on bus 1, and is loaded into the D/A converter buffer by a WR signal on line 32. An EN1 signal on line 33 then renders gate 42 conductive for the desired duration, or pulse width, and the output signal is produced at the first output. The program then loads a new pulse amplitude value into the D/A converter, and the gate enabling sequence is performed on gate 44 to produce the selected pulse at the second output. After pulse output is complete, the REFG signal is dropped, and all zeroes are loaded into the D/A converter. The LCD data is restored on bus 1 for the display, and the foreground program continues. Pulse output comprises a major portion of the foreground program's time, since output pulses can range from 30 to 250 microseconds in duration.

The program next checks to see if the count of the rate counter is two. If so, sentinel pulses must now be produced, in advance of the output pulses five milliseconds later. Again, the LCD data on bus 1 is stored so that bus 1 can be used to transfer pulse amplitude values to the D/A converter. The program checks to see if the amplitude of the upcoming pulse for the first output will be greater than 4 milliamperes as referenced to an internal milliampere scale. If not, no sentinel is needed, since the output pulses themselves are too low to result in any patient hazard. But if the output pulse is to be greater than 4 ma., a sentinel pulse with a 5 ma. amplitude and a 30 $\mu$sec. duration is produced at the first output, using the same output sequence described above. This process is repeated to generate a sentinel pulse at the second output.

If an electrode has come loose from the patient as detected by the comparator 52, an interrupt will have occurred at the INT input. If the interrupt has occurred, a sentinel-detected failure flag is set in a register R2. During the following pass through the foreground program, this flag in register R2 will be detected, the LED will turn on, and the output pulse sequence will be bypassed.

Continuing on in FIG. 6C, a ½ second counter is decremented. A number of functions occur at half-second intervals. If the ½ second counter is at zero, it is reinitialized and a treatment time flag is set. During treatment, the patient sees treatment time on the display in elapsed time up to 255 minutes. Treatment time is accumulated in half-second intervals by the background program in response to the setting of the treatment time flag.

A half-second flag is also cleared. To prevent a patient from producing needlessly high amplitude pulses by ramping the output pulse amplitude up too quickly, the pushbuttons that permit the pulse parameters to be changed are allowed to produce a step change only once each half-second. This half-second flag allows these time increments to be monitored by the background program. When a parameter pushbutton is held down, the parameter will change by one increment every half second.

A sample mode switch flag is also cleared. This flag tells the background program to interrogate the mode switch every half second. More frequent interrogation has not been found to be helpful or necessary, and in fact reduces the time during which other functions may be performed.

After the ½ second counter is queried, the mode is again checked to see if the burst mode has been selected. If it has, the burst counter is decremented and checked to see if it is at zero. If so, it is reinitialized and the burst flag is set so that a new sequence of seven burst pulses will be produced beginning with the next pass through the foreground program.

The foreground program is now completed, and the register bank Ø for the background program is selected. The accumulator is restored to the contents it had at the beginning of the foreground sequence, and the system resumes with the background program at the point where it was before the foreground timer interrupt occurred.

Figure 7:
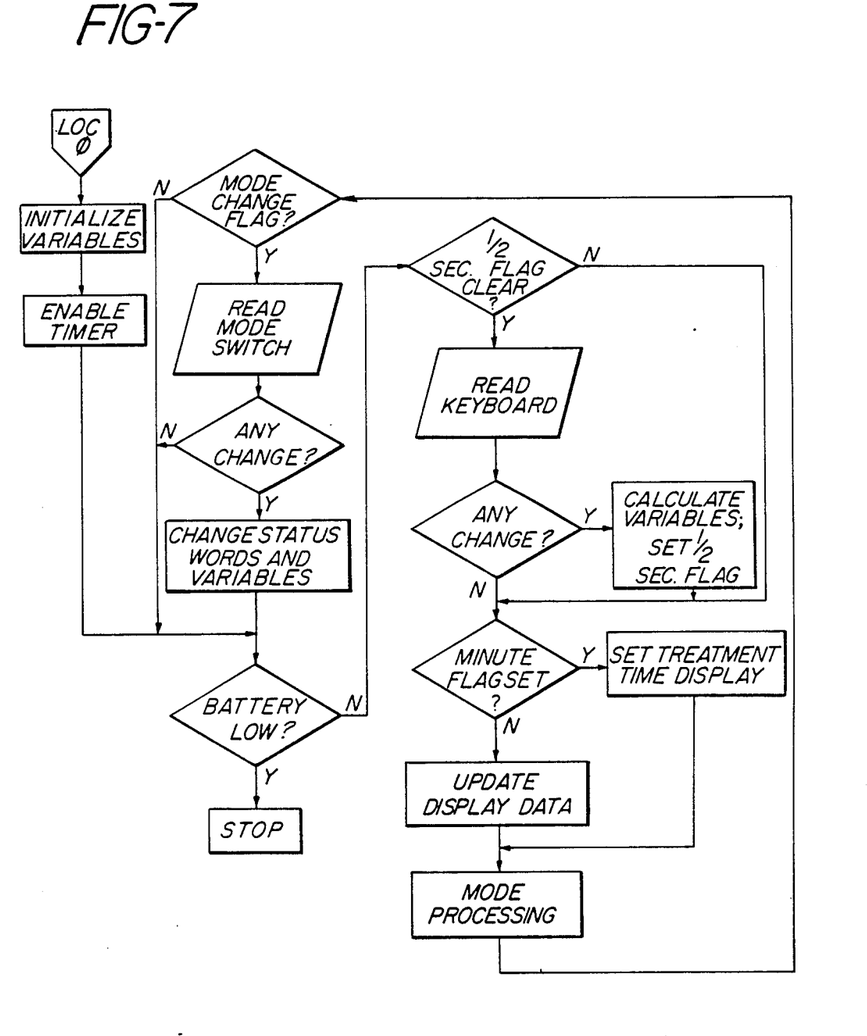

The background program is shown in the flowchart of FIG. 7. When the stimulation device is turned on, the microprocessor is reset and the background program starts from location zero. Several variables are intitialized; pulse amplitude is set to zero, pulse width is set at 50 μsec., and the rate is set at 80 Hz. The sentinel is cleared and counters are initialized. The internal timer for the foreground program is enabled with its initial count of 240.

The background program then checks the battery voltage. If it is low, the program stops and the LED is lit. If the battery voltage is at a sufficient level, the program checks to see if the one-half second flag has been cleared by the foreground program. If the flag has been cleared, the background program reads the keyboard buttons DISP, INC, and DEC, and looks for any change. If the flag has not yet been cleared, a half second has not passed since the last button was pushed, and the keyboard is not read. If a new button entry is detected, the program decodes and notes it, and calculates the appropriate new variables for storage in the RAM. After this calculation, the one-half second flag is reset, to be cleared by the foreground program after one-half second has been counted down.

The background program then checks to see if a minute flag has been set. During treatment, the program records and displays treatment time in minutes. Treatment time is tracked in one-half second increments. When a full minute has been accumulated, the treatment time display is incremented to the next minute, up to a maximum of 255 minutes. During treatment this time is flashed periodically to inform the user that treatment is progressing normally. The off time during flashing extends the life of the display.

After the minute flag is checked and found not to be set, the data for the LCD display is calculated and loaded into the appropriate locations in the RAM for access by the foreground program. As mentioned above, the LCD display waveforms must be inverted every 20 msec, in synchronism with the change of state of the LCD backplane pulse train of 25 Hz.

Thereafter, the background program does processing necessary according to the mode of operation. If treatment is proceeding in the normal or the strength-duration mode, the program proceeds to the mode interrogation sequence of the program. If the device is in the burst mode, the program checks to see if the burst sequence of seven pulses has been completed. If the device is in the modulation mode, the program calculates the parameters of the next pulse if the appropriate flag has been set by the foreground program. If the device is in the calibration portion of the strength-duration mode, the program calculates any needed pulse widths, amplitudes, and the logarithmic curve for pulse characteristics. After these calculations, the program proceeds to the mode interrogation sequence.

The modulation and strength-duration modes of operation are more fully described in concurrently filed U.S. patent application Ser. No. 617,444, entitled "TREATMENT PULSE SEQUENCES FOR A TRANSCUTANEOUS NERVE STIMULATION DEVICE".

The background program next checks to see if the sample mode switch flag has been cleared by the foreground program. If it hasn't, the program drops down to the battery check step. If the flag has been cleared, the program reads the mode switch. If there has been a mode change, the program changes any status words for the mode processing sequence, including the flag, and initializes variables for parameter values. The background program then proceeds to the battery check step.

Figure 8:
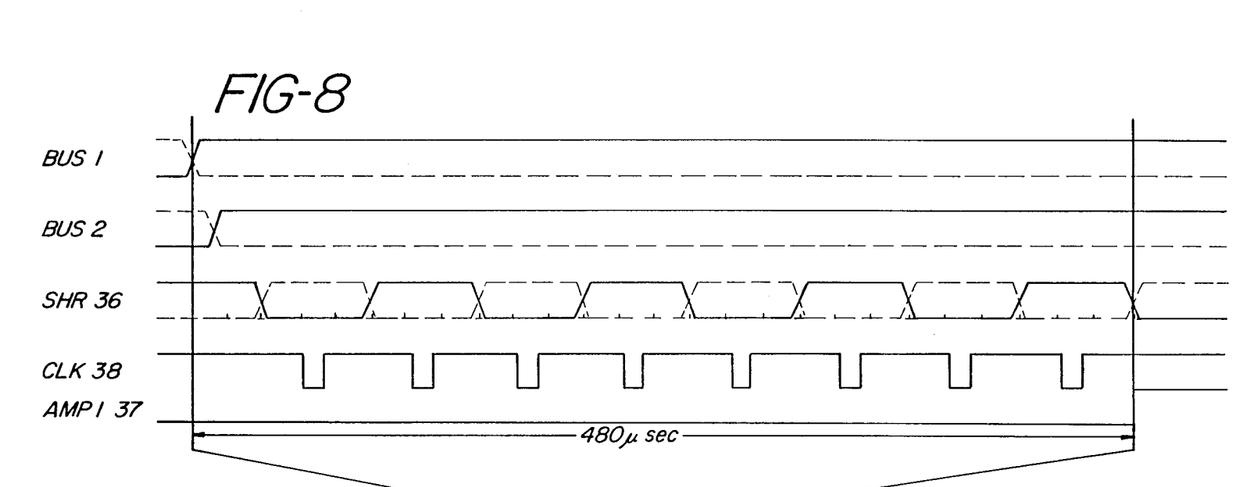
FIGS. 8-13 are timing diagrams illustrative of the operation of the stimulation device of FIG. 1.
Figure 9:
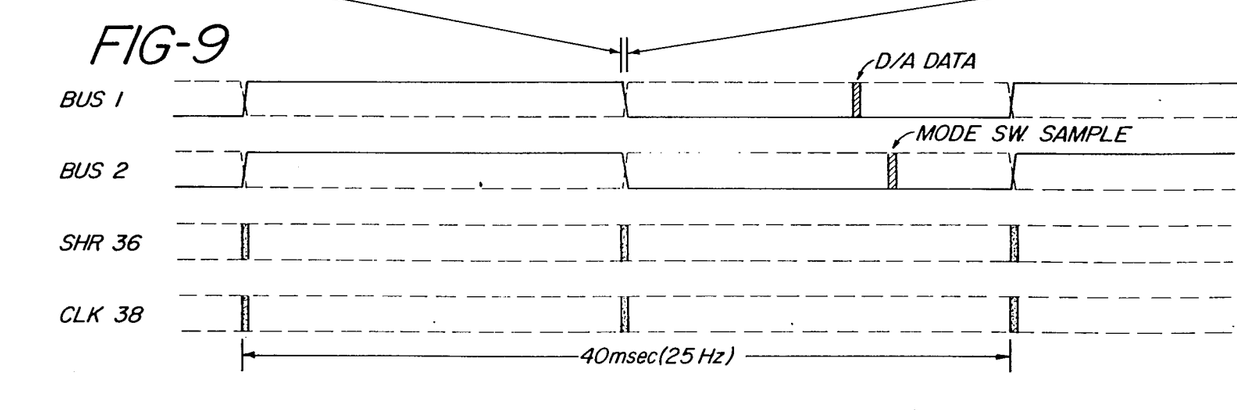

It should be remembered that the foreground program is continually interrupting the background program every time the internal times counts an interval of 2.5 milliseconds. The pulse waveforms of FIGS. 8–13 illustrate how the buses of the microprocessor are being time-shared to provide different functions. The waveforms of FIG. 8 show a 480 microsecond interval during which time the LCD data for the display is updated. Referring concurrently to FIG. 3, the data values on buses 1 and 2 are updated as needed at the beginning of the 480 microsecond interval to control the segments of the right-hand and center digits of the LCD display. Line 36 sends out a sequence of eight pulses (SHR), which are clocked into shift registers 22a and 22b by CLK pulses on line 38. The control line 37 for the AMP1 display is also changed as needed.

The 480 microsecond interval of FIG. 8 is related to the 25 Hz pulse waveforms which occur continuously on the buses 1 and 2 for the LCD data. A full 25 Hz cycle takes 40 milliseconds, and it can be seen that the level changes and shift register loading occurs at the transition times of the 25 Hz waveforms. At other times, the signal levels on buses 1 and 2 are stable, except for the similarly short asynchronous intervals when output data is sent to the D/A converter 40, and the mode switch is sampled. In the sequencing shown in FIGS. 8 and 9, the LCD characters are changed without any noticeable change or flicker.

Figure 10:
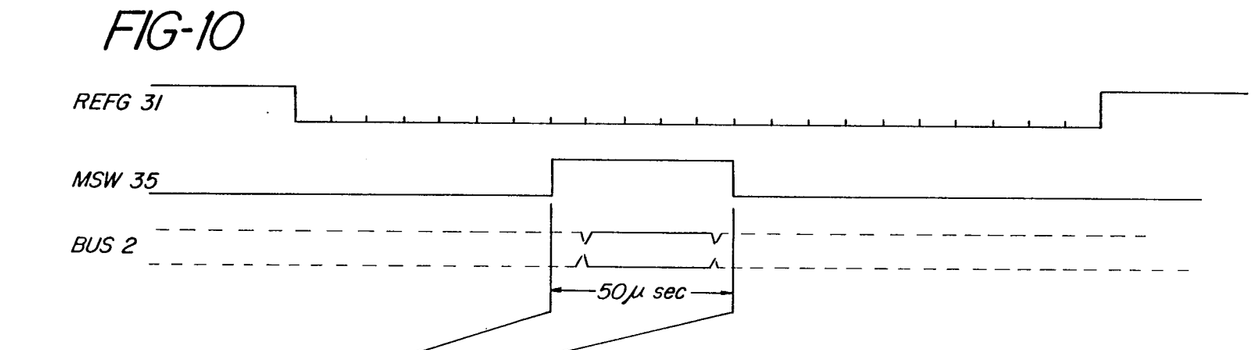
Figure 11:
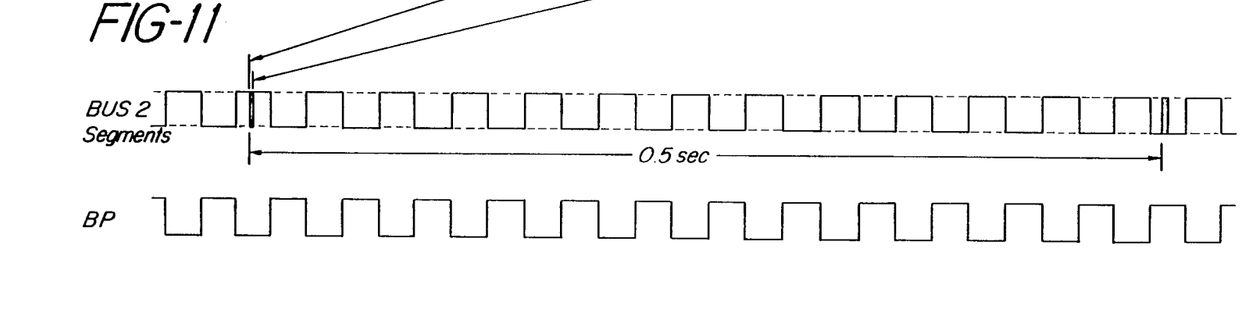

FIGS. 10 and 11 relate the timing of the battery check and mode switch interrogation to the LCD waveforms. In FIG. 10, the REFG pulse on line 31 is applied to the regulator transistor 118 in FIG. 3 to turn on the regulated voltages while the battery voltage is checked. A MSW pulse on line 35 is applied to transistor 74 for 50 microseconds to apply a low level signal to the left-hand terminals of the mode switch 24. The arm of the mode switch then connects this low level to one of the lines of bus 2, which is controlled by the microprocessor as an input bus during this time. The microprocessor will detect a low signal on the line of bus 2 connected to the appropriate right-hand mode switch terminal. All other lines will be in a high state.

This sampling of the battery and mode switch occurs only every half second, and therefore has no significant impact on the LCD display. At all other times, bus 2 is an output bus to the LCD display 20. This is seen in FIG. 11, where the mode sampling periods are related to the 25 Hz waveforms normally on bus 2.

The lower waveform, BP, is the backplane pulse train on bus line P25. When the BP signal is in phase opposition to a segment signal, as is the case of the solid bus 2 waveform of FIG. 11, a voltage is impressed across the segment and a dark LCD segment appears. When the bus signal is controlled to be in phase with the BP signal, no voltage is applied across the segment and the segment cannot be seen.

Figure 12:
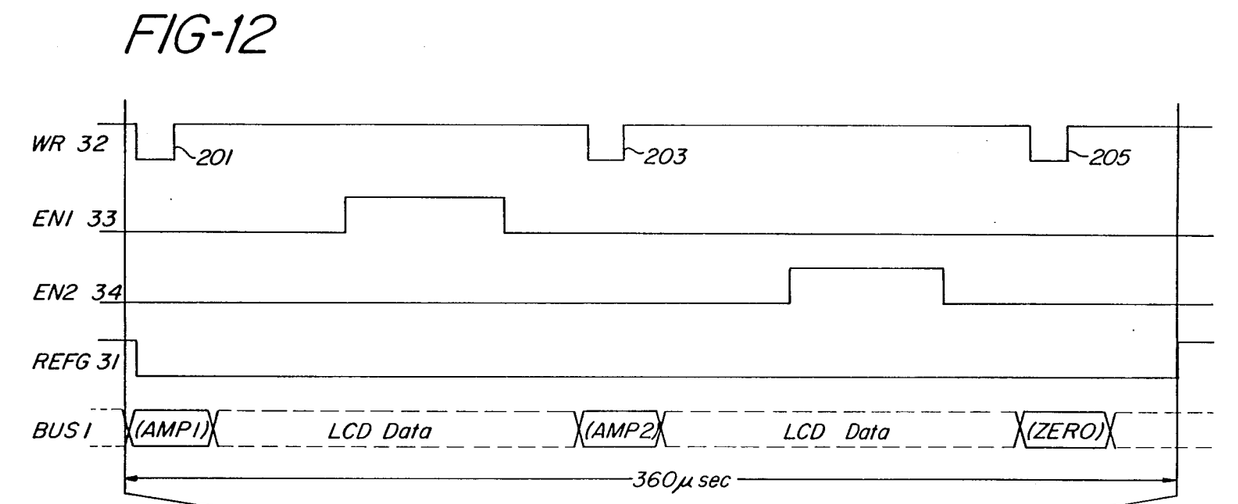
Figure 13:
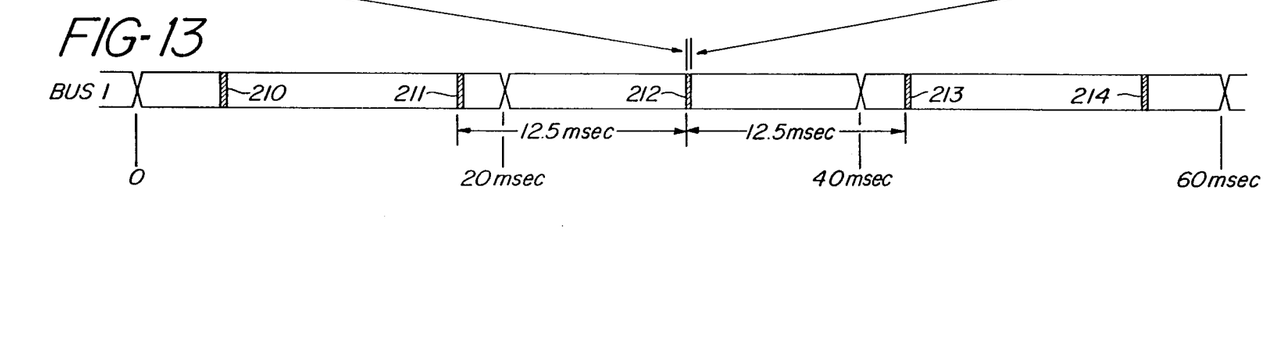

FIGS. 12 and 13 relate the pulse output sequence to the 25 Hz LCD waveforms. In FIG. 12, a typical sequence is shown for an 80 pulse per second rate sequence of 50 microsecond width pulses. The sequence is 360 microseconds in length in this example. At first, a REFG signal on line 31 applies a reference voltage to the D/A converter 40. A pulse amplitude value for the first output (AMP1) is put out on bus 1 and is loaded into the D/A converter buffer by a WR pulse 201 on line 32. An EN1 pulse on line 33 then closes gate 42 for the pulse width time, 50 microseconds, and an output pulse at the first output is produced for the duration of the EN1 pulse. A second WR pulse 203 then loads the pulse amplitude value for the second output (AMP2) into the D/A converter. An EN2 pulse on line 34 closes gate 44 for the required pulse width, and an output pulse is produced at the second output. Finally, a third WR pulse 205 loads a zero value pulse amplitude into the D/A converter, and the REFG pulse ends, removing the reference voltage from the D/A converter.

In FIG. 13, these 360 microsecond output pulse sequences are related to the 25 Hz waveforms. Output sequences 210-214 recur every 12.5 milliseconds for the 80 pulse per second rate of this example. The 25 Hz waveform is seen to change polarity every 20 milliseconds. The 360 microsecond interruptions are so rapid relative to the 25 Hz clock that the user sees no flicker in the LCD display. Moreover, as shown in FIG. 12, the LCD data values are restored to the bus 1 between every loading of the D/A converter.

In use of the stimulation device of the present invention, a user places the electrodes on the treatment area of the body. The desired mode is selected by setting the mode switch, and the ON/OFF switch is turned on. The left AMP indicator for output 1 is displayed first, and the user then increments (INC) or decrements (DEC) the pulse amplitude value using the appropriate buttons. The DISP button is pressed and PW for the first output is displayed. The user then pushes the INC and DEC buttons to set the desired pulse width. A further push of the DISP button displays the RATE indication, and the INC and DEC buttons are pressed to set the desired pulse rate. The DISP button is pressed two more times and the amplitude and pulse width for the second output are displayed and adjusted in the same manner. The pulse rate is common to the two outputs.

The amplitude values are calibrated over a range of 0-50 ma., and can be incremented and decremented in 1 ma. steps. The pulse width is variable over a range of 30-250 microseconds in steps of 10 microseconds. The rate is variable from two to one hundred Hertz, with selections being 2 Hz, 100 Hz, and 10-80 Hz in steps of 10 Hz.

What is claimed is:

1. A portable transcutaneous nerve stimulation device for producing therapeutic electrical stimulation pulses comprising:
   battery means for energizing the circuitry of said device;
   a microprocessor having inputs and outputs;
   memory means, connected to said microprocessor, which retains a program for enabling said microprocessor to control treatment pulse production and treatment parameter display in a time-shared manner;
   output pulse circuitry having an input coupled to outputs of said microprocessor and an output at which treatment pulses are produced;
   a display having inputs coupled to ones of said outputs of said microprocessor and continuously responsive to signal levels at said outputs of said microprocessor for displaying treatment parameters; and
   means for applying treatment parameters to an input of said microprocessor.

2. The stimulation device of claim 1, wherein said memory means retains software program means for controlling said microprocessor, partitioned into a background program means and a foreground program means,
   wherein said background program means comprises means for calculating output signals for said display and for said output pulse circuitry, and wherein said foreground program means comprises means for controlling the timing of operation of said output circuitry and said display.

3. The stimulation device of claim 2, wherein said treatment parameter means includes a plurality of switches which are periodically sampled by said software program means.

4. The stimulation device of claim 3, wherein said treatment parameter means includes a mode switch which is set to control the mode of operation of said device, the setting of said mode switch being periodically sampled by said software program means.

5. The stimulation device of claim 1, wherein said output pulse circuitry includes a digital to analog converter, and wherein said display comprises a liquid crystal display; and
   wherein said microprocessor has an output bus coupled to inputs of said digital to analog converter and to inputs of said liquid crystal display.

6. The stimulation device of claim 5, wherein said microprocessor comprises means for producing control signals for said display on said output bus, said display signal production being interrupted periodically for the production of output pulse control signals on said output bus.

7. The stimulation device of claim 4, wherein said microprocessor has a data bus coupled to said mode switch and to said display, said data bus being controlled by said microprocessor as an output bus for applying control signals for said display, and as an input bus for periodically sampling the setting of said mode switch.

8. The stimulation device of claim 1, wherein said output circuitry includes a digital to analog converter having an output, a control input, and data inputs coupled to outputs of said microprocessor, and a transmission gate having an input coupled to the output of said digital to analog converter, an output coupled to an output of said device, and a control input;

said microprocessor having a first control line coupled to said control input of said digital to analog converter for causing the production of an output voltage by said converter, and a second control line coupled to said control input of said transmission gate for rendering said gate conductive during the production of a treatment pulse.

9. The stimulation device of claim 8, further including a second transmission gate having an input coupled to the output of said digital to analog converter, an output coupled to a second output of said device, and a control input;

wherein said microprocessor has a third control line, coupled to said control input of said second transmission gate, for rendering said second transmission gate conductive during the production of a treatment pulse at said second output.

10. The stimulation device of claim 8, wherein said digital to analog converter further includes a reference voltage input, wherein said microprocessor controls the application of a reference voltage to said reference voltage input during the production of treatment pulses.

11. A portable transcutaneous nerve stimulation device for producing therapeutic electrical stimulation pulses comprising:

battery means for energizing the circuitry of said device;

an output at which treatment pulses are produced;

a display for displaying parameters of said treatment pulses;

controller means having an output bus and producing control signals for said output and said display on said output bus at different times during treatment, said controller having input lines;

memory means, coupled to said controller means, for storing a program for operating said controller means for the production of treatment pulses and the display of parameters on said display;

means for coupling said display to said output bus, wherein said display is continously responsive to signals on said bus for displaying parameters in accordance with said signals;

means for coupling said output to said output bus in common with said display, wherein said output is selectively responsive to signals on said bus for the production of treatment pulses; and means for applying treatment pulse parameter signals to said input lines of said controller means for control of said treatment pulse parameters and for display of pulse parameters on said display.

12. The stimulation device of claim 11, wherein said controller means is a digital microprocessor.

13. The stimulation device of claim 12, wherein said output bus comprises a digital bus on which output control signals and display control signals are produced in a time-shared manner by said microprocessor.

14. The stimulation device of claim 11, wherein said display comprises a liquid crystal display controlled by signals produced by said controller means; and wherein said output includes a digital to analog converter which is responsive to signals produced by said controller means.

15. The stimulation device of claim 14, wherein lines of said output bus are coupled to both inputs of said digital to analog converter and to segment control inputs of said liquid crystal display.

16. The stimulation device of claim 11, wherein said output includes a digital to analog converter having an output, and an input coupled to said output bus of said controller means;

a gate having an input coupled to the output of said digital to analog converter, and an output at which treatment pulses are produced, wherein said gate is coupled to an output line of said controller means for controllably rendering said gate conductive during the production of said treatment pulses.

17. The stimulation device of claim 11, wherein said treatment pulse parameter means comprises a plurality of switches coupled to said input lines of said controller means.

18. The stimulation device of claim 17, wherein said treatment pulse parameter means further includes a mode switch for selecting a mode of operation of said device, said mode switch being connected to an input line of said controller means.

* * * * *